(12) United States Patent
Chow

(10) Patent No.: US 6,969,525 B2
(45) Date of Patent: Nov. 29, 2005

(54) SURGICALLY IMPLANTED TIME RELEASE MEDICATION FOR POST-SURGICAL TREATMENT OF A PATIENT

(75) Inventor: James C. Y. Chow, 4121 Veterans Memorial Dr., Mount Vernon, IL (US) 62864

(73) Assignee: James C. Y. Chow, Mount Vernon, IL (US)

( * ) Notice: Subject to any disclaimer, the term of this patent is extended or adjusted under 35 U.S.C. 154(b) by 277 days.

(21) Appl. No.: 10/165,549

(22) Filed: Jun. 8, 2002

(65) Prior Publication Data

US 2003/0228356 A1    Dec. 11, 2003

(51) Int. Cl.$^7$ ............................ A61K 9/00; A61K 9/48; A61F 13/00
(52) U.S. Cl. ...................... 424/423; 424/489; 424/422; 424/426; 424/443; 514/21
(58) Field of Search ................................ 424/422, 423, 424/424, 426, 443, 444, 489; 530/356, 342; 514/21

(56) References Cited

U.S. PATENT DOCUMENTS

| | | | |
|---|---|---|---|
| 4,990,144 A | 2/1991 | Blott | |
| 5,741,685 A | 4/1998 | Vacanti | |
| 5,830,173 A | 11/1998 | Avery et al. | |
| 5,919,473 A * | 7/1999 | Elkhoury | 424/422 |
| 6,448,378 B2 | 9/2002 | DeVore et al. | |
| 2004/0142013 A1 * | 7/2004 | Rubsamen | 424/423 |

* cited by examiner

Primary Examiner—Gary Kunz
Assistant Examiner—Mina Haghighatian
(74) Attorney, Agent, or Firm—Polster, Lieder, Woodruff & Lucchesi

(57) ABSTRACT

A method of administering a medication to a post operative patient with the medication being administered at the site of a surgery performed on the patient. The medication is formed into a time release capsule (10) having a core (12) of the medication which is dispensed within the body over a predetermined period of time. The capsule is covered with a coating (14) that dissolves within the body. The time release medication is not released until the covering is sufficiently dissolved to expose the medication. During surgery, the surgeon places placing a plurality of capsules (10–10$n$) in the patient's body at the surgery site. The respective capsules have different coating thicknesses so the medication contained therein is dispensed at different periods of time after the surgery as a function of the thickness of the coating.

5 Claims, 2 Drawing Sheets

SURGICALLY IMPLANTED TIME RELEASE MEDICATION FOR POST-SURGICAL TREATMENT OF A PATIENT

CROSS REFERENCE TO RELATED APPLICATIONS

None

STATEMENT REGARDING FEDERALLY SPONSORED RESEARCH OR DEVELOPMENT

Not applicable

BACKGROUND OF THE INVENTION

This invention relates to the treatment of patient's in post-surgery; and in particular, to the use of timed release medication to prevent blood clots and infections, control pain and facilitate healing, and to also control high blood pressure, and treat diabetes and other possible complications to which the surgical patient is subjected.

Major surgeries, for example, hip replacement and knee replacement surgeries involve a lengthy healing process. During this period, and especially during the early stages of recovery, great care must be taken to insure that blood clots do not form in the area where the surgery was performed, and that infection does not set in. Since these surgeries can also involve a lot of pain, pain control is also important in facilitating recovery. Narcotics are also often given the patient to relieve pain, particularly at the site of the incision. Narcotics, of course, can be addictive.

In addition, some patients suffer from conditions (high blood pressure, diabetes, for example) which can affect the patient's recovery. While the patient is still hospitalized, doctors and nurses are available to monitor their condition and provide immediate treatment if conditions warrant. Most patients, however, leave the hospital well before recovery is over and complete their recovery at home. They still usually see their doctor on a periodic basis to insure their progress goes well. During the early stages of recovery, while still hospitalized, the post-operative patient is given periodic injections of appropriate drugs to prevent clotting and infections, and to facilitate the healing process. Or, the patient is hooked to a catheter by which measured doses of medication are periodically administered. In some instances, self-contained infusion pumps are implanted to dispense the medication. While the injections and catheterization is uncomfortable, patients understand they are necessary and put up with the pain and discomfort. When the patient leaves the hospital, he or she is given prescriptions for appropriate oral medications they can take at home to continue their recovery. Once at home, the patient may still receive injections from a visiting nurse.

Injections are painful. Catheters are inconvenient. Taking medication can be overlooked or forgotten. Because the surgery is major surgery, the possibility of complications is substantially greater than might normally be the case. Since the doctor's primary concern is the welfare and complete recovery of the patient, the doctor has an interest in seeing that the patient receives all the medication they require. Accordingly, a delivery system that allows the doctor to conveniently provide required medications, while insuring the patient receives the appropriate dosages over the period of time he or she is both in the hospital and after they leave, would be beneficial.

BRIEF SUMMARY OF THE INVENTION

The present invention is directed to a medication delivery system involving surgically implanted time release medication for post-surgical treatment of a patient. The medication comprises capsules of medication with a coating or covering being of a variable thickness. The capsules are implanted in the patient's body during surgery at the site of the operation. Capsules with a thinner layer of coating will release their medication at one time, and capsules with a thicker coating will release their medication at a later time. The delivery system can include more than one type of medication. By varying the thickness of the capsule coatings, dosages can be released at specific times (hours and days) after the operation. Use of the capsules eliminates the need for post-surgery injections or catheters, while insuring that adequate medication is given to the patient. The delivery system can be employed with any type of major surgery.

The delivery system could eliminate the need for prescriptions to be taken after the patient leaves the hospital, and injections given by the nurse. It can also eliminate the need for the administration of narcotics to ease the patient's pain since an anesthetic can be continuously administered, reducing the attendant risk of addiction.

Other objects and features will be in part apparent and in part pointed out hereinafter.

BRIEF DESCRIPTION OF THE SEVERAL VIEWS OF THE DRAWINGS

The objects of the invention are achieved as set forth in the illustrative embodiments shown in the drawings which form a part of the specification.

Corresponding reference characters indicate corresponding parts throughout the several views of the drawings.

DETAILED DESCRIPTION OF INVENTION

The following detailed description illustrates the invention by way of example and not by way of limitation. This description will clearly enable one skilled in the art to make and use the invention, and describes several embodiments, adaptations, variations, alternatives and uses of the invention, including what I presently believe is the best mode of carrying out the invention. As various changes could be made in the above constructions without departing from the scope of the invention, it is intended that all matter contained in the above description or shown in the accompanying drawings shall be interpreted as illustrative and not in a limiting sense.

Figure 1:
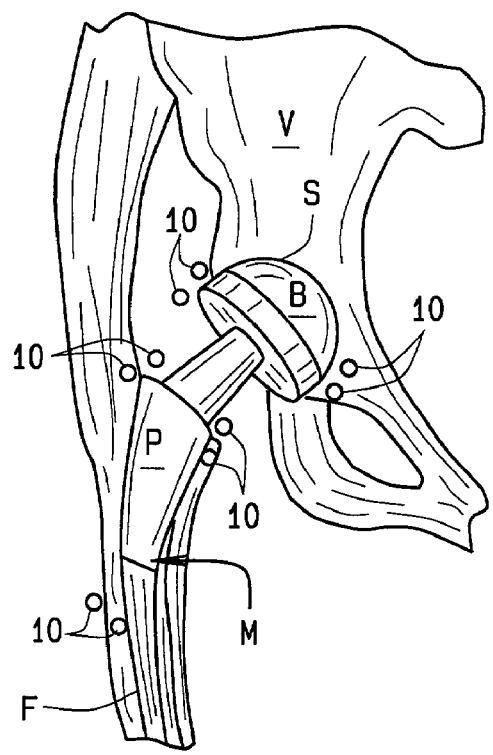
FIG. 1 is a simplified representation of a hip transplant.

Referring to the drawings, FIG. 1 is a simplified representation of a hip replacement. As shown in the figure, the damaged upper end of the thighbone (femur) F is removed and replaced by a prosthesis P. A ball B end of the prosthesis is fitted into a socket (acetabulum) S of the pelvis V. A stem end M of the prosthesis is fitted into the femur.

Figure 2:
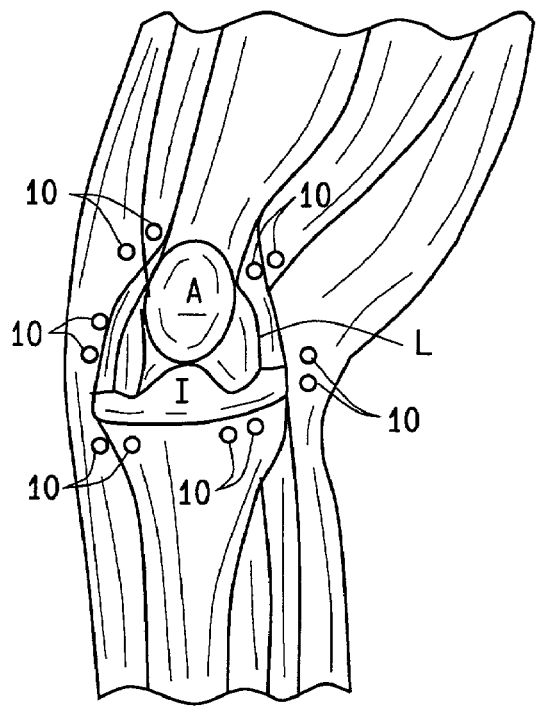
FIG. 2 is a simplified representation of a knee transplant.

FIG. 2 is similar to FIG. 1 but illustrates a knee replacement. Here, the prosthesis typically consists of a femoral component L usually made of metal, a patellar component R usually made of plastic, and a tibial spacer component T also usually made of plastic. In this operation, the orthopedic surgeon removes damaged cartilage and bone, inserts the prosthetic components, and positions and aligns them to restore proper functioning to the knee.

The design, construction, and functioning of the hip and knee replacement prostheses form no part of the present invention.

Those skilled in the surgical arts will understand that performing these and other major surgeries require the surgeon to cut into muscle tissue, and remove and reshape bone and other tissue. Two major complications associated with such surgeries first include infections in the joints where the prostheses are fitted, and the surrounding bone and muscle tissue. The second is blood clots forming in the veins carrying blood to the lower body, particularly the legs, and the veins surrounding the operating site. In addition, diabetics and people with high blood pressure or other related illnesses present additional problems during recovery.

Figure 3:
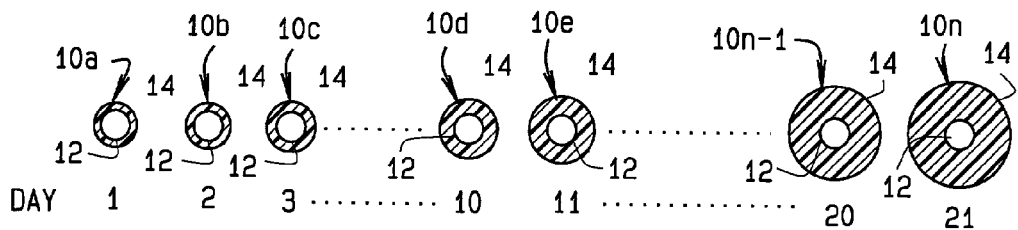
FIG. 3 is a cross-section of a series of time release capsules of the present invention which are implanted in a person during hip or knee replacement surgery, and other types of major surgery.

In accordance with the present invention, a time release medication is provided for post-surgical treatment of a patient. As shown in FIG. 3, the medication includes time release capsules 10a–10n which are placed in the body, at the surgical site, by the surgeon performing the operation. The capsules contain a prescribed dosage of an anti-coagulant, antibiotic, pain killers, and other drugs which prevent complications from occurring or assists the healing process. Accordingly, each capsule includes a core 12 of a pharmaceutical. The core, in turn, is covered by a coating 14 of varying thickness. The number of capsules deposited in the body by the surgeon is a function of the amount of time of the patient's recovery. In FIG. 3, twenty-one capsules are indicated for a twenty-one day recovery period. The core 12 of each capsule is the same size so that the same dosage is to be given each day. The covering, however, becomes increasingly thicker. The overall thickness of the covering is a function of the amount time it takes for normal bodily processes to disintegrate the shell; it being understood that it will take longer to dissolve thicker layers of covering than thinner layers. Further, the core 12 of medication need not be, and preferably is not, released all at once when the covering is finally sufficiently dissolved to expose the core. Rather, the medication contained in the core is released over a defined period, for example, twenty-four hours. In this embodiment, the amount of medication contained in each capsule is uniform.

As a result, when using the time release medication of the present invention, the surgeon "salts" the operating site with the time release capsules sometime during the surgical procedure. At the completion of the surgery, the patient is given anti-coagulants, antibiotics, pain killers, and other drugs as appropriate. Now, one day after the surgery, the covering of capsule 10a dissolves to where core 12 of the medication is exposed and this medication is now released into the patient's body. Forty-eight hours after surgery, the medication in the core of capsule 10a is completely absorbed into the patient's body. Now, the cover of capsule 10b is sufficiently dissolved so core 12 of this capsule is exposed. Again, the medication contained in core 12 is released. After seventy-two hours from the surgery, the medication in the core of capsule 10b is completely dissolved. At this time, the covering 14 of capsule 10c is dissolved to where the medication in core 12 of the capsule is exposed, and the medication release process is repeated. The process continues for as many days as there are time release capsules implanted in the body. It could be the twenty-one day period as indicated in FIG. 3, or a longer or shorter period of time.

Significantly, the method of the invention insures proper medication in appropriate dosages is administered to the patient throughout the recovery period. Any discomfort experienced by the patient due to the presence of the capsules disappears as the capsules are absorbed by the body. At the same time, the need for injections or catheterization is substantially eliminated, as is the need to give medication to the patient to take once he or she leaves the hospital. Also, because the amount of medication administered to the patient is both time limited and carefully controlled, the risk of addiction to certain types of medication is substantially eliminated.

Figure 4:
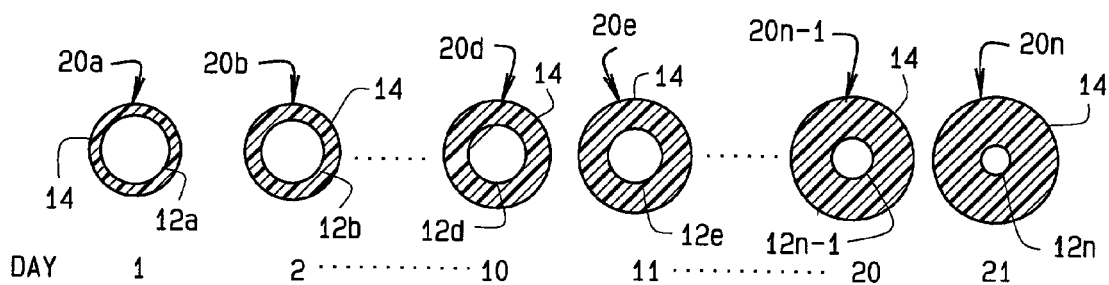
FIG. 4 is a similar cross-section of time release capsules comprising a second embodiment of the invention; and, FIG. 5 is a cross-section of time release capsules comprising a third embodiment of the invention.

Referring to FIG. 4, a second embodiment of the time release capsules of the invention are indicated generally 20a–20n. As with the capsules shown in FIG. 3, the capsules 20 are round, spherically shaped capsules. Unlike the capsules 10 previously described in which the core 12 of medication was for the same dosage, in this embodiment, the amount of medication contained in the capsules 20 varies. For example, in the early stages of recovery, more medication may be administered on a daily basis than during the later stages of recovery. Accordingly, the size of core 12 may get increasingly smaller while the size of the capsule covering 14 increases.

Figure 5:
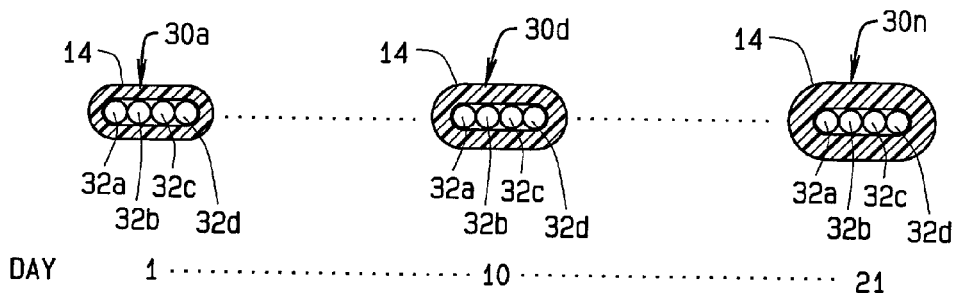

Referring to FIG. 5, a third embodiment of the invention includes elongated capsules 30, rather than round capsules as shown in FIGS. 3 and 4. In addition, dosages of different medications 32a–32d are contained in each capsule 30a–30n. Or, the medication may be the same, but are time released over a given period. Thus, when the covering over capsule 30a dissolves, a pain killer, for example, is released over the next six-hour period by unit 32a contained in the capsule. Then, for the six-hour period after that, the pain killer in unit 32b is released. And so forth with respect to units 32c and 32d. Thus, the medication is administered continuously over the course of a day. Again, the covering 14 on the capsules increase in thickness from the capsule 30a whose contents are to be released the first day after surgery, through capsule 30d whose contents are released on the tenth day, through capsule 30n whose contents are released the twenty-first day after surgery.

There are a number of other variations with respect to the administering of time release medication using the method of the present invention. For example, one form a medication can be released by capsules during a first period of the recovery, and a second form during the latter stages. To accomplish this, in a first series capsules, for days one-ten for example, core 12 of the capsule is the one form of the medication. In accordance with the invention, and as shown in FIG. 3, the thickness of covering 14 is such that successive capsules are used up each of the first ten days with the one form of the medication being time released when the covering of the capsule is sufficiently dissolved to expose the core. Beginning with the eleventh capsule, and extending through the twenty-first day, a second form of the medication is administered as the capsules dissolve.

In another embodiment of the invention, the medication does not have to be time released, but can be completely delivered when the covering of the capsule is sufficiently dissolved to expose the core of medication. It will be understood by those skilled in the art that two delivery systems can therefore be employed at the same time. In one delivery system, one type of medication is time released over a given period; while with the other delivery system, the medication is dispensed all at once.

As shown in FIGS. 1 and 2, the capsules are not necessarily concentrated in one area, but rather are distributed throughout the surgical site. A group of capsules (twenty-one day's worth using the previous example) can be placed by the surgeon at a number of locations at the operating site. As part of the preparation for the surgery, packets of capsules are prepared containing an appropriate number for each of the medications to be administered over the recovery time. Then, during the surgery, the surgeon empties the contents of the packets at appropriate locations. In this regard, the capsules can be color coded. So, for example, capsules containing antibiotics are contained in capsules of one color, those containing anti-coagulants in capsules of another color, those containing pain killers in a third color, and so forth. The surgeon is then able to readily determine what medications he is packing into the operating site. Again it will be appreciated by those skilled in the art that the surgeon can pack more medication into one surgical area than another. This can be done by placing more capsules in the packet emptied at the one site, or the surgeon may empty multiple packets of the same medication at the site.

In accordance with the above described procedure, the method of the invention also includes placing more than one capsule for the same medication at a given location. If it is desirable, for example, to deliver 100 mg of a medication each twenty-four hour period, then the surgeon can use one 100 mg capsule for each day, or two 50 mg capsules, or four 25 mg capsules, etc. In this same regard, if the dosage is to be decreased over time, then the packet containing the capsules would contain X number of capsules of a given dosage for one period of time, Y number of capsules for a second period of time, etc. Capsules containing the same medication, but of different dosages can also be color coded so the surgeon can readily tell what dosages of a medication are being implanted at a location.

Lastly, it will be understood by those skilled in the art that the delivery system of the present invention can be used with any major surgery. So, in addition to replacement surgery, the method of the invention can be used in chest, back, abdominal, thoracic, and other surgeries. Importantly, a major advantage of the delivery system of the invention is the ability to concentrate medication such as a pain killer at the site of the surgery, and particularly the area around where incisions were made. These areas tend to be particularly painful and the pain is now often treated with injections of a narcotic. The ability to place capsules of a pain killer right at the site of the incision, provides a local concentration that may eliminate the need to use narcotics to relieve the pain. Not subjecting the patient to the possibility of becoming addicted is very beneficial.

In view of the above, it will be seen that the several objects and advantages of the present invention have been achieved and other advantageous results have been obtained.

What is claimed is:

1. A method of administering a medication to a post operative patient with the medication being administered at the site of a surgery performed on the patient, comprising:
   incorporating the medication in a time release capsule for the medication to be dispensed within the body over a period of time;
   covering the capsule with a coating dissolved within the body, the medication being released when the covering is sufficiently dissolved to expose the medication, and,
   placing a plurality of capsules having different thicknesses of coating in the patient's body at the surgery site during the surgery for the medication contained therein to be dispensed into the patient's body at different periods of time after the surgery as a function of the thickness of a capsule's coating, the dosages contained in respective capsules varying with capsules having a higher dosage of medication having a thinner coating than those capsules having a thicker coating whereby a capsule containing a higher dosage of medication releases its medication into the patient's body sooner after the surgery than a capsule with a thicker coating and a lower dosage of medication, and the patient receives medication over a prolonged period of time.

2. The method of claim 1 in which all of the capsules contain the same dosage of the medication.

3. The method of claim 2 in which all the capsules contain the same type of medication.

4. The method of claim 1 wherein some of the capsules contain a first type of medication, and other of the capsules contain a second type of medication, the first and second types of medication being released at different points in time during a post operative period.

5. The method of claim 1 in which each capsule contain at least two different types of medication.

* * * * *